(12) United States Patent
Cliche et al.

(10) Patent No.: US 6,865,007 B2
(45) Date of Patent: Mar. 8, 2005

(54) COMPLEX FREQUENCY RESPONSE FILTER AND METHOD FOR MANUFACTURING THE SAME

(75) Inventors: Jean-François Cliche, Charlesbourg (CA); Michel Têtu, Cap-Rouge (CA); Christine Latrasse, Québec (CA); Alain Zarka, Val-Bélair (CA)

(73) Assignee: Dicos Technologies Inc., Quebec (CA)

( * ) Notice: Subject to any disclaimer, the term of this patent is extended or adjusted under 35 U.S.C. 154(b) by 0 days.

(21) Appl. No.: 10/391,483

(22) Filed: Mar. 18, 2003

(65) Prior Publication Data

US 2004/0047041 A1 Mar. 11, 2004

Related U.S. Application Data

(60) Provisional application No. 60/365,159, filed on Mar. 19, 2002.

(51) Int. Cl.[7] ................................................ G02F 1/07
(52) U.S. Cl. ..................... 359/260; 359/263; 359/264
(58) Field of Search ................. 359/260, 263, 359/264, 278, 267, 245, 239, 238, 578, 580, 584, 585, 589

(56) References Cited

U.S. PATENT DOCUMENTS 5,499,256 A * 3/1996 Bischel et al. ............... 372/28
6,600,588 B2 * 7/2003 Kawanishi .................. 359/246
2002/0181106 A1  12/2002 Xia et al. .................... 359/578
2002/0181107 A1  12/2002 Cook ........................... 359/578

FOREIGN PATENT DOCUMENTS

EP    0991152 A3    10/2001
EP    1052745 A3    10/2001

* cited by examiner

*Primary Examiner*—Tim Thompson
(74) *Attorney, Agent, or Firm*—Fogg & Associates LLC; Laura A. Ryan

(57) ABSTRACT

There is provided a complex frequency response filter providing a frequency response having a desired shape. A first complex frequency response filter includes a first and a second reflecting surfaces defining a resonant cavity therebetween. Each of the reflecting surfaces respectively has a predetermined surface finish providing a given reflectivity, therefore providing resonances with a predetermined shaped frequency response of a predetermined amplitude and of a predetermined periodicity. Those frequency responses can then be summed to generate an arbitrarily complex spectral response. In another embodiment, the complex frequency response filter includes a transmission medium and a first and a second reflecting surfaces defining a resonant cavity therebetween. The transmission medium has a predetermined transmission pattern distributed therein therefore providing resonances having a predetermined shaped frequency response of a predetermined amplitude and of a predetermined periodicity, which can be combined to generate arbitrary frequency responses. A method for manufacturing such devices is also disclosed.

14 Claims, 4 Drawing Sheets

COMPLEX FREQUENCY RESPONSE FILTER AND METHOD FOR MANUFACTURING THE SAME

CROSS REFERENCE TO RELATED APPLICATIONS

This application is related to and claims the benefit of the filing date of provisional application Ser. No. 60/365,159 (the "'159 application"), filed on Mar. 19, 2002. The '159 application is incorporated by reference

FIELD OF THE INVENTION

The present invention generally relates to optical devices and more particularly concerns a complex frequency response filter and a method for manufacturing such a complex frequency response filter.

BACKGROUND OF THE INVENTION

Wavelength division multiplexed (WDM) communication system offer a high data transmission capacity by allowing multiple laser sources to transmit many high-speed data channels simultaneously into a single fiber, where each channel is transmitted at a unique optical frequency (or wavelength). In order to standardize the frequencies of the channels across telecommunication systems, the industry has adopted a standard which specify that the nominal optical frequency of every channel should be at an integer multiple of 100 GHz, 50 GHz, 25 GHz or even smaller spacings. The absolute frequencies accuracy must typically be within 2.5 GHz or 1.25 GHz, or even better for those systems with the highest channel densities.

Semiconductor lasers currently used in telecommunication systems do not intrinsically generate frequencies accurate or stable enough to be used alone in such a frequency grid system, whether they are narrowly or widely tunable lasers. This is caused by many reasons. First, current fabrication technologies do not permit to know with sufficient accuracy the nominal frequency of the lasers with respect with the frequency tuning signal. Second, the frequency of the laser varies significantly with operating conditions and environmental factors such as temperature. Third, even if all other parameters are kept constant, the frequency of a laser tend to drift with aging. All these factors can easily detune a laser frequency beyond the accepted limit during its lifetime.

Various means have been devised to stabilize the frequency of semiconductors to a predetermined value with a sufficient accuracy. Many of those use an optical frequency reference element which is sufficiently accurate and stable for the telecommunication applications. This reference element is used to compare the frequency of the laser with the predetermined value and generate an error signal which is fed back to the laser to correct its frequency. Once the feedback system is operational and the laser is frequency-locked, the stability of the reference is transferred to the laser.

Fabry-Perot resonators are often used in telecommunication devices in order to provide regularly-spaced frequency reference points over a broad range of frequencies. High-finesse resonators display narrow transmission peaks that can be used to accurately pinpoint specific frequencies, while between these peaks there is a zone where transmission is weak and show little variations. On the opposite, low-finesse resonators do not display sharp peaks but rather wide and flat peaks, with a transmission that varies periodically and continuously from peak to peak. Low-finesse resonators are useful when it is needed to know how far the frequency of a source is from the center of the peak by measuring the transmission of the resonator.

There are some applications where both a high finesse and low finesse resonator would be useful. For example, while locking a laser to a resonator peak, a low finesse would allow the laser to have a wide locking range, and once the laser is locked, a high-finesse would be needed to provide high locking accuracy.

Therefore, it would be advantageous to provide a single resonator simultaneously displaying the advantages of high and low finesse resonators, since high finesse peaks allow accurate frequency pinpointing and locking, and a low finesse peaks allows to extend the locking range and also allows frequency interpolation.

Other applications may require to have a device which display a more complex frequency response than a simple Fabry-Perot resonator can provide and yet have a device that generate this frequency response repeatedly over a large frequency range. It would therefore be advantageous to provide a complex frequency response filter providing a frequency response having a desired shape.

SUMMARY OF THE INVENTION

It is an object of the present invention to provide a complex frequency response filter that satisfies the above mentioned needs.

Accordingly, there is provided a complex frequency response filter including a first and a second reflecting surfaces defining a resonant cavity therebetween. Each of the reflecting surfaces respectively has a predetermined surface finish providing a given reflectivity, therefore providing resonances with a predetermined shaped frequency response of a predetermined amplitude and of a predetermined periodicity.

Accordingly, there is also provided a complex frequency response filter including a transmission medium and a first and a second reflecting surfaces defining a resonant cavity therebetween, The transmission medium has a predetermined transmission pattern distributed therein therefore providing resonances having a predetermined shaped frequency response of a predetermined amplitude and of a predetermined periodicity.

It is preferable object of the present invention to provide a complex frequency response filter which implements a Fabry-Perot resonator displaying simultaneously high finesse peaks to allow accurate frequency pinpointing and locking, and a low finesse valleys which allows to extend the locking range and also allows frequency interpolation.

Accordingly, there is provided a complex frequency response filter wherein the predetermined periodicities are equal to each other.

It is another object of the present invention to provide a method for manufacturing a complex frequency response device.

BRIEF DESCRIPTION OF THE DRAWINGS

These and other objects and advantages of the invention will become apparent upon reading the detailed description and upon referring to the drawings in which.

Figure 1:
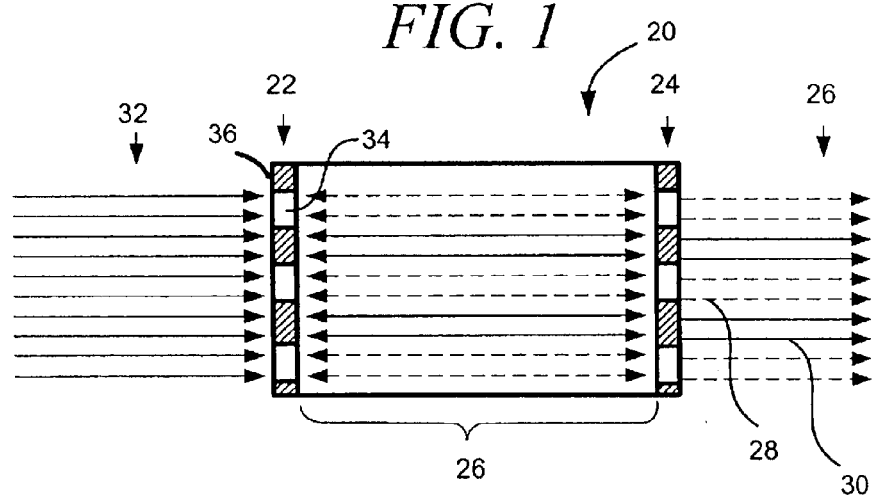
FIG. 1 is a side sectional view of a complex frequency response filter according to a preferred embodiment of the present invention.

While the invention will be described in conjunction with an example embodiment, it will be understood that it is not intended to limit the scope of the invention to such embodiment. On the contrary, it is intended to cover all alternatives, modifications and equivalents as may be included as defined by the appended claims.

DESCRIPTION OF PREFERRED EMBODIMENTS OF THE INVENTION

In the following description, similar features in the drawings have been given similar reference numerals and in order to weight down the figures, some elements are not referred to in some figures if they were already identified in a precedent figure.

The present invention concerns a complex frequency response filter and a method for manufacturing such a filter. Referring to FIG. 1, there is shown a first preferred embodiment of a complex frequency response filter 20 including a first and a second reflecting surfaces 22, 24 defining a resonant cavity 26 therebetween displaying a plurality of transmission or reflections peaks. Each of the reflecting surfaces 22, 24, which are preferably parallel to each other, respectively has a predetermined surface finish providing a given reflectivity (or equivalently optical losses). The surface finish of the reflecting surfaces 22, 24 preferably includes several low reflectivity regions 34 and high reflectivity regions 36. The reflectivity of the surfaces determines the finesse of the filter, that is, determines how narrow the transmission peaks are. Thus, the surface finish is such that the reflection coefficient is not identical over the whole facet reflecting surfaces, which causes the cavity to produce a filtered light beam 26 having a first part 28 and a second part 30 displaying various finesses.

Each of said reflecting surfaces 22, 24 is preferably a planar mirror, but a curved mirror can also be envisaged as well as a combination of a planar and a curved mirror. Moreover, the reflecting surfaces 22, 24 preferably extend in a substantial parallel relationship.

Each of the parts 28, 30 of the filtered light beam 26 respectively has a predetermined shaped frequency response of a predetermined amplitude and of a predetermined periodicity. In the illustrated embodiment, two different reflectivity values are used and therefore, generate a filtered light beam 26 that has two parts 28, 30 with distinct frequency responses. Of course, any number of different reflectivity value could be used, according to a particular application.

If the output light 26 is collimated into a fiber or is detected by a photodetector, low and high frequency responses will be summed and will provide a particular periodic frequency response. The reflecting surfaces 22, 24 may be arranged to be immovable, thereby providing an etalon filter. However, one can imagine that the optical distance between the two reflecting surfaces 22, 24 is tunable for providing a tunable filter 20. Or special electro-optic or other voltage or temperature sensitive materials (such as liquid crystals) or devices could be used to change the reflectivity of the reflecting surfaces with time. The filter 20 may also be advantageously provided with a tuning mechanism, such for non-restrictive example, a Thermo Electric Cooler. It should be noted that the light signal passing through the filter 20, as well as the reflected light signal can be used.

Figure 2:
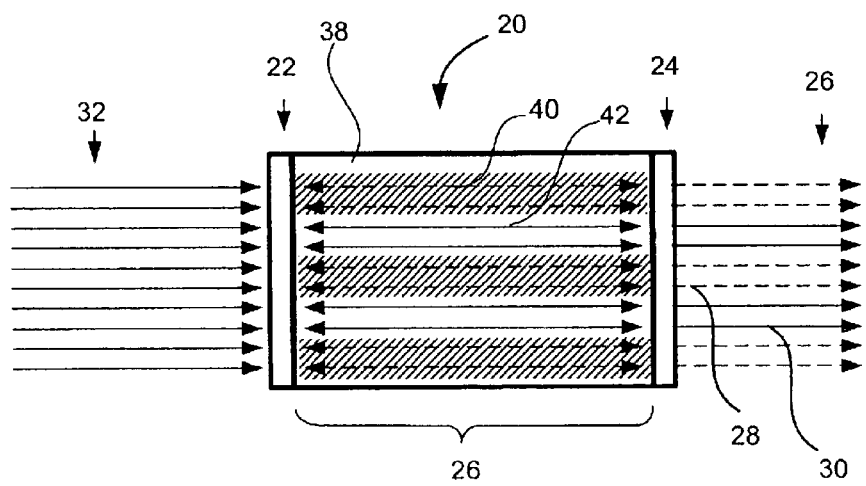
FIG. 2 is a side sectional view of another complex frequency response filter according to another preferred embodiment of the present invention.

Referring now to FIG. 2, there is shown a second preferred embodiment of another complex frequency response filter 20 including a transmission medium 38 and a first and a second reflecting surfaces 22, 24 defining a resonant cavity 26 therebetween. The transmission medium 38 has a predetermined transmission pattern distributed therein providing a filtered light beam 26 comprising a first part 28 and a second part 30. Each of the parts 28, 30 experiences different resonance properties due to the different optical losses they experience in the cavity. Each of the parts 28, 30 therefore respectively has a predetermined shaped frequency response of a predetermined amplitude and of a predetermined periodicity. In this preferred embodiment, each of the reflecting surfaces 22, 24 has a uniform reflectivity pattern but the resonator transmission medium 38 has different regions 40, 42 with high or low optical transmission, thereby generating high and low finesse resonances. As in the previously described embodiment, low and high frequency responses will be summed and will provide a particular periodic frequency response. Of course any number of different optical transmission regions could be used for providing a multiple finesse filter.

In fact, each of the complex frequency response filters 20 illustrated in FIGS. 1 and 2 implements a Fabry-Perot resonator displaying simultaneously high and low finesse peaks which can be combined to generate the desired frequency response. In another preferred embodiment which is not illustrated, the different parameters, such as the position of the reflecting surfaces, the ambient temperature or other physical parameters can be controlled, thereby providing a filter whose complex frequency response can be dynamically tuned.

Figure 3:
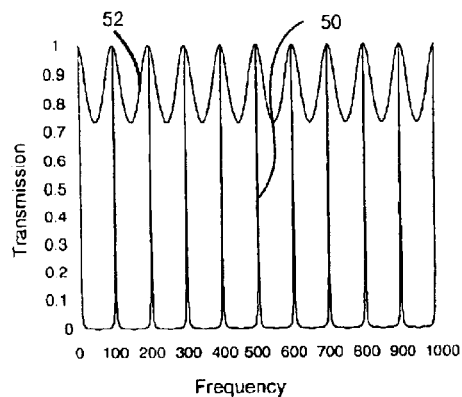
FIG. 3 is a graph illustrating the frequency response of a complex frequency response filter according to a preferred embodiment of the present invention.
Figure 4:
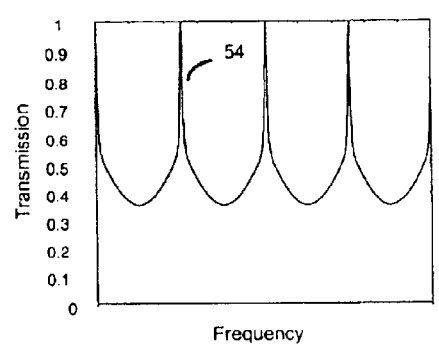
FIG. 4 is a graph illustrating the frequency response of a complex frequency response filter according to another preferred embodiment of the present invention.

FIGS. 3 and 4 illustrates how to sum the outputs of different resonating regions with two different finesses in order to produce a complex frequency response. This particular response allows interpolation and accurate peak pinpointing. In this particular embodiment, each of the predetermined periodicity of the shaped frequency responses is equal to each other. This provides a single FSR. Of course different periodicities could also be envisaged for providing the desired frequency response. In that case, the filter present different FSR. Combining filters with slightly different FSR would allow to generate filters which have a very long resulting periodicity.

Indeed, with reference to FIG. 3, the graph 50 illustrates the light transmission versus frequency of a high finesse filter. This, however, has the disadvantage that there is no transmission between two adjacent peaks, and this makes it difficult to estimate how far the laser is from a transmission peak if it happens to be away from the narrow peak. In some other occasion, it is necessary to have a filter, or a combination of filters, which present a low finesse. The graph 52 illustrates the transmission of such a low finesse resonator. With such a resonator, there is a measurable transmission signal in most of the frequency spectrum, therefore allowing large locking range and allow using the amplitude values to estimate how far a laser source is from a peak. A low finesse filter does not permit however to have a high accuracy when a laser is locked to it since the transmission peak is wide.

The present invention thus provides a filter which has both a high and low finesse in order to benefit from the advantages from both types of filters. The resulting curve 54 shown in FIG. 4 is then a combination of the low and high finesse curves. Another advantage of the present invention is that, since the frequency responses are produced by the same filter, they are coupled and track each other when environmental changes or tuning occur.

Figure 16:
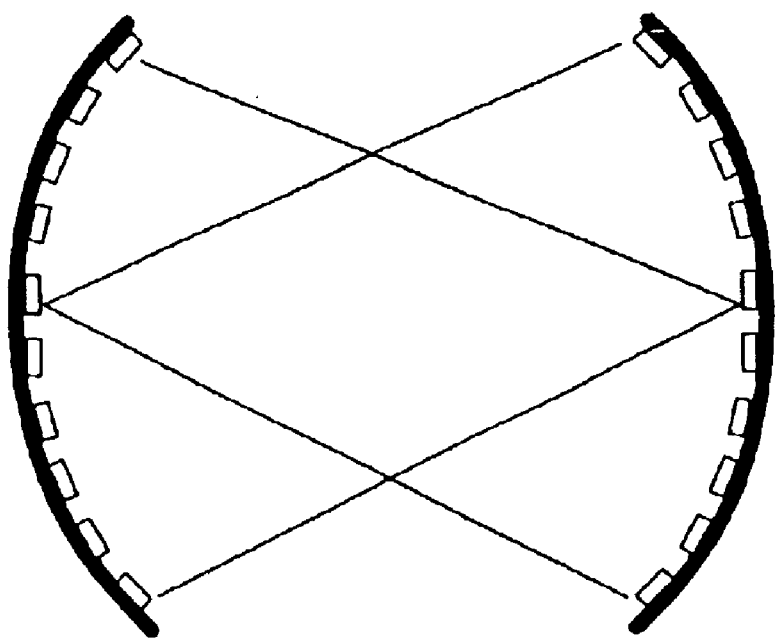
FIG. 16 is a side sectional view of another complex frequency response filter according to another preferred embodiment of the present invention.

Various types of resonators can be used with the proposed technique. Ring resonators, spherical mirror resonators, confocal/planar resonator or any other kind of resonator geometry commonly known in the art could be adapted to display local resonating properties which, once detected as a single summed, may generate any arbitrary frequency response. FIG. 16 illustrates such a resonator which is made of concave mirrors with different reflectivity regions on their surfaces.

The resonator may include reflective surfaces are absorbing material which have frequency-dependent properties. This would provide more degrees of freedom in designing a resonator with arbitrary spectral responses.

FIGS. 5 to 8 illustrates some examples of how the different reflectivity patterns can be distributed on the reflecting surfaces 22, 24 to obtain two different finesses on the same filter. Many other patterns can be exploited to achieve the same results. For example, a random reflectivity pattern may be envisaged. As already explained, this technique can also be used on filters implemented with concave reflecting surfaces instead of flat reflecting surfaces. Of course, the same technique can be used to create a filter 20 which simultaneously display more than two finesses values. This can be done by increasing the number of reflectivity values used in the reflecting surface reflectivity patterns.

Figure 5:
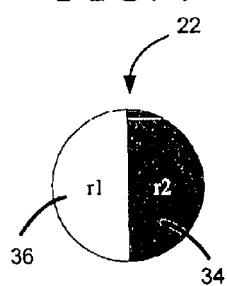
FIG. 5 illustrates a predetermined distributed reflectivity pattern of a reflecting surface according to a preferred embodiment of the present invention.
Figure 6:
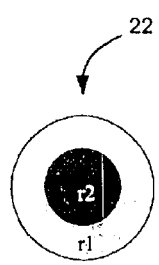
FIG. 6 illustrates another predetermined distributed reflectivity pattern of a reflecting surface according to another preferred embodiment of the present invention.
Figure 7:
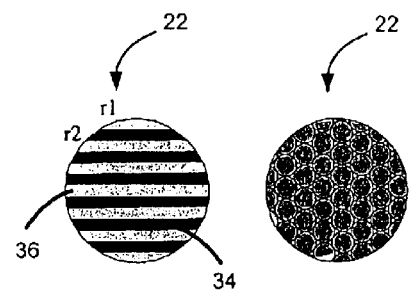
FIG. 7 illustrates another predetermined distributed reflectivity pattern of a reflecting surface according to another preferred embodiment of the present invention.
Figure 8:
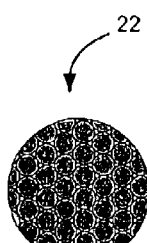
FIG. 8 illustrates another predetermined distributed reflectivity pattern of a reflecting surface according to another preferred embodiment of the present invention.

Referring particularly to FIG. 5, one can separated two regions with a straight demarcation line. Thus The light power entering each regions is substantially the same.

Figure 9:
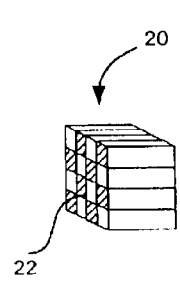
FIG. 9 is a side and front elevation view of a complex frequency response filter wherein the reflecting surface shows a predetermined reflectivity pattern.
Figure 10:
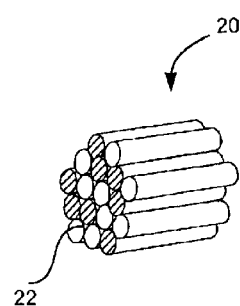
FIG. 10 is a side and front elevation view of another complex frequency response filter wherein the reflecting surface shows a predetermined reflectivity pattern.
Figure 11:
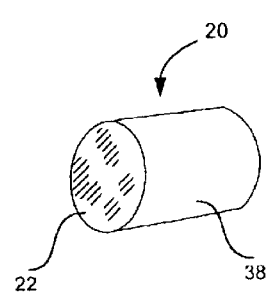
FIG. 11 shows the complex frequency response filter of FIG. 10 which has been fused according to another preferred embodiment of the present invention.

FIGS. 9 to 10 illustrates how to create a resonator having different finesses by combining various resonators having reflecting surfaces provided with a predetermined distribution pattern. These individual filters can be advantageously fused to produce the filter of FIG. 11. In another embodiment, various reflectivity substances can be placed directly on the surface of an uniform filter 20.

Figure 12:
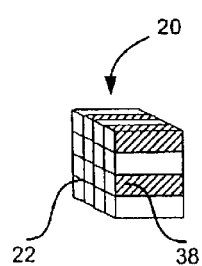
FIG. 12 is a side and front elevation view of a complex frequency response filter wherein the transmission medium shows a predetermined reflectivity pattern.
Figure 13:
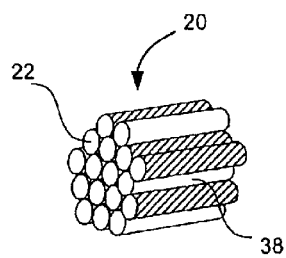
FIG. 13 is a side and front elevation view of another complex frequency response filter wherein the transmission medium shows a predetermined reflectivity pattern.
Figure 14:
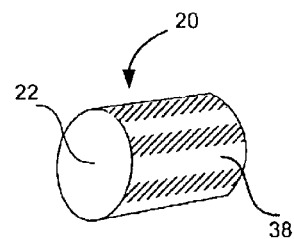
FIG. 14 shows the complex frequency response filter of FIG. 13 which has been fused according to another preferred embodiment of the present invention.

FIGS. 12 to 14 illustrates how various resonators with different optical losses and therefore different finesses can be combined to achieve the same result. In another preferred embodiment, lossy substances could be implanted in the bulk of a uniform filter 20 to create various lossy regions. These individual filters can be advantageously fused to produce the filter of FIG. 14.

Figure 15:
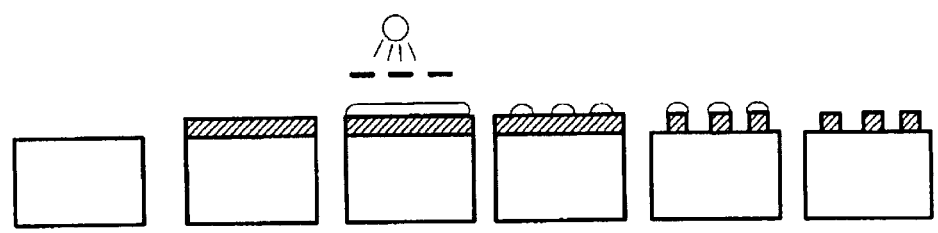
FIG. 15 illustrated a photolithographic process for creating a reflecting surfaces according to a preferred embodiment of the present invention.

Referring now to FIG. 15, there is shown the different steps of a photolithographic process that can be used for providing a predetermined reflectivity distribution pattern on the reflecting surfaces 22, 24. In this process, one can successively deposed reflecting material patterns on different regions on the reflecting surface. Many other processes can also be conveniently used. For example, different reflecting patterns can be created by a high precision machining in removing the reflecting coating on different regions. In another example, absorbent substances can be printed on the reflecting surface for providing different reflectivity and different losses. In another process, one can depose a uniform reflecting coating and locally affect the reflectivity of different regions by photolithographic process, ion implantation, electron-beam scribing or chemical deposition. Another possibility is to etch in certain regions, patterns, which are smaller than the wavelength of the incoming light beam, on a uniform reflecting surface for modified the average reflectivity which is seen by the wave front. Another possibility is to fused different filters having different finesse. One can also use substrates presenting different absorption levels along their length. These substrates are placed in a parallel relationship and can be fused together or glued. Then, one can machine parallel faces. Another possibility is to locally dope a substrate with different absorbent substances.

In a preferred embodiment, each of the reflecting surfaces is a metallic thin film made of, for example, aluminum, gold, tin or silver. This preferred embodiment provides a filter having a large band. In another preferred embodiment, the reflecting surfaces are dielectric mirrors consisting of a plurality of successive layers having known refractive indices. This embodiment does not provide a large band filter but allows to reduce losses. A typical resonator is generally provided with 3 mm×3 mm faces. Thus, the reflecting surfaces are preferably 0.5 mm large.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

What is claimed is:

1. A complex frequency response filter comprising a first and a second reflecting surfaces defining a resonant cavity therebetween, wherein:

each of said reflecting surfaces respectively has a predetermined surface finish providing given reflectivity causing a resonance, each of said resonance parts respectively having a predetermined shaped frequency response of a predetermined amplitude and of a predetermined periodicity.

2. The complex frequency response filter according to claim 1, wherein each of said surface finish respectively has a predetermined distributed reflectivity pattern.

3. The complex frequency response filter according to claim 1, wherein each of said reflecting surfaces is obtained by a photolithographic process.

4. The complex frequency response filter according to claim 1, wherein each of said predetermined periodicities is equal to each other.

5. The complex frequency response filter according to claim 1, wherein each of said reflecting surfaces comprises a planar mirror.

6. The complex frequency response filter according to claim 1, wherein each of said reflecting surfaces comprises a curved mirror.

7. The complex frequency response filter according to claim 1, wherein said first reflecting surface comprises a planar mirror and said second reflecting surface comprises a curved mirror.

8. The complex frequency response filter according to claim 1, wherein said reflecting surfaces extend in a substantially parallel relationship.

9. The complex frequency response filter according to claim 1, wherein said reflecting surfaces are immovable, thereby providing a Fabry Perot Etalon.

10. The complex frequency response filter according to claim 1, wherein an optical distance between said two reflecting surfaces is tunable.

11. A complex frequency response filter comprising a transmission medium and a first and a second reflecting surfaces defining a resonant cavity therebetween, wherein:
said transmission medium has a predetermined transmission pattern distributed therein providing a filtered light beam comprising a first part and a second part, each of said parts respectively having a predetermined shaped frequency response of a predetermined amplitude and of a predetermined periodicity.

12. The complex frequency response filter according to claim 11, wherein each of said reflecting surfaces respectively has a predetermined surface finish having a distributed reflectivity pattern.

13. The complex frequency response filter according to claim 11, wherein each of said predetermined periodicities is equal to each other.

14. A complex frequency response filter comprising a first and a second reflecting surfaces defining a resonant cavity therebetween, wherein:
each of said reflecting surfaces respectively has a predetermined surface finish providing a filtered light beam comprising a first and a second part, each of said parts respectively having a predetermined shaped frequency response of a predetermined amplitude and of a predetermined periodicity.

* * * * *